United States Patent
Truscott et al.

(10) Patent No.: US 9,149,500 B2
(45) Date of Patent: Oct. 6, 2015

(54) METHOD AND PROCESS FOR RELIEVING OR PREVENTING SYMPTOMS

(71) Applicants: Kent J. Truscott, Hercules, CA (US); Susan M. Abernathy, Hercules, CA (US)

(72) Inventors: Kent J. Truscott, Hercules, CA (US); Susan M. Abernathy, Hercules, CA (US)

(*) Notice: Subject to any disclaimer, the term of this patent is extended or adjusted under 35 U.S.C. 154(b) by 0 days.

(21) Appl. No.: 13/998,314

(22) Filed: Oct. 21, 2013

(65) Prior Publication Data

US 2014/0044811 A1 Feb. 13, 2014

Related U.S. Application Data

(62) Division of application No. 12/150,515, filed on Apr. 28, 2008, now abandoned.

(51) Int. Cl.
*A61K 36/736* (2006.01)
*A61K 36/00* (2006.01)
*A61K 33/00* (2006.01)
*A61K 36/23* (2006.01)

(52) U.S. Cl.
CPC .............. *A61K 36/736* (2013.01); *A61K 33/00* (2013.01); *A61K 36/23* (2013.01)

(58) Field of Classification Search
CPC .............................. A61K 36/23; A61K 36/736
See application file for complete search history.

(56) References Cited

U.S. PATENT DOCUMENTS

| | | | | |
|---|---|---|---|---|
| 2001/0002269 A1* | 5/2001 | Zhao | | 426/112 |
| 2001/0002407 A1* | 5/2001 | Nair et al. | | 514/886 |
| 2002/0137691 A1* | 9/2002 | Murad | | 514/23 |
| 2007/0065456 A1* | 3/2007 | Woods | | 424/195.17 |
| 2011/0287117 A1* | 11/2011 | Schlesinger | | 424/735 |

FOREIGN PATENT DOCUMENTS

| | | | |
|---|---|---|---|
| CN | 1965858 A | * | 5/2007 |
| WO | WO00/40258 | * | 7/2000 |
| WO | WO 2008016823 A2 | * | 2/2008 |

OTHER PUBLICATIONS

Website document entitled: "Herbs-wholesale.com". 2006. Retrieved from the internet on Jan. 25, 2010. (available at: http://www.herbs-wholesale.com/cherryfruitextract-2466.html). pp. 1-3.*
Website document entitled "Dealing with Gout". Retrieved from internet on Jan. 27, 2010 (available at: http://hsibaltimore.com/2004/01/28dealing -with-gout/). Jan. 28, 2004. pp. 1-4.*
Website document entitled: "The Medicine Man's Corner". Web Archive 2005. Retrieved from internet on Jan. 25, 2010. (availabile at: http://www.themedicineman.com/store/merchant.mvc?Screen=PROD&Product_Code=068958045153&Category_Code=).*
Nuki et al. (2006) Arthritis Research and Therapy, 8(Suppl 1): S1-5.*
Lans (2006) J. Ethnobiology and Ethnomedicine 2:45.*
Lee et al. (2006) Current Rheumatology Reports 8: 224-230.*
Sundy et al. (2007) Current Rheumatology Reports 9: 258-264.*
Mohammad Najmul Ghani Khan, Khazaain-al-Advia, vol. III, Page(s) being submitted-05 (p. 04-08) ( Ref.p. no.of publication:98 ), 1926, Nadeem Yunus Printer / Sheikh Mohd Basheer & Sons, Lahore.†
Abu Bakr Mohammad.Bin Zakariyya Al-Razi, Kitaab-al-Haawi-fil-Tibb, vol. XI, Page(s) being submitted-04 ( p. 09-12), ( Ref.p. no.of publication:105-106 ), 1962, Dayerah-al-Ma'aarif Usmania, Hyderabad, India.†
Swami Harsaranananda Vaidya, Asava Vijnan, Page(s) being submitted-06 (p. 13-18) ( Ref.p. no.of publication:101 ), 3rd edition 2000, The Punjab Ayurvedic Pharmacy, Amritsar, India.†

* cited by examiner
† cited by third party

*Primary Examiner* — Chris R Tate
*Assistant Examiner* — Russell Fiebig
(74) *Attorney, Agent, or Firm* — Susan M. Abernathy

(57) ABSTRACT

A method for relieving or preventing symptoms associated with uric acid crystals, comprising consuming a formulation that supports three or more processes, the processes comprising:
1) one that inhibits formation of uric acid in the body;
2) one that increases elimination of uric acid from the body; and
3) one that interferes with formation of uric acid crystals in the body.

Also, a process to make a formulation, comprising mixing together:
  i. a material that inhibits formation of uric acid in a body;
  ii. a material that increases elimination of uric acid from the body;
  iii. a material that interferes with formation of uric acid crystals in the body; and forming the mixture into a medicament.

13 Claims, No Drawings

METHOD AND PROCESS FOR RELIEVING OR PREVENTING SYMPTOMS

FIELD OF THE INVENTION

This invention is directed to a method for relieving or preventing symptoms associated with uric acid crystals, a formulation for relieving or preventing symptoms associated with uric acid crystals, a process to make the formulation, and the formulation made by the process.

BACKGROUND OF THE INVENTION

Uric acid is an end product of nitrogen metabolism in the human body (the main product being urea), and is found in small amounts in blood and urine. The disease 'gout' in humans is associated with abnormally high levels of uric acid in the blood and in the urinary system and with the formation of uric acid crystals in or near the joints. The symptoms caused by uric acid crystals include redness, swelling, inflammation, pain, kidney stones, and reduced movement. Increased concentration of uric acid in the human blood stream may also result in one form of kidney stones when the uric acid crystallizes into a solid inside the kidney. The uric acid crystals are made of salts of urate anions and cations including ammonium, sodium, potassium, calcium and magnesium. Ammonium urate is a uric acid crystal that often forms stones or uroliths in the urinary system. Sodium urate is a uric acid crystal that often causes symptoms in or near the joints in gout.

Medications such as NSAIDs, corticosteroids and allopurinol are commonly used to treat gout. These medications are effective, but have significant adverse side-effects. None of these medications are known to be mixed together into a single medicament.

Since the 1800s, colchicine has been a standard treatment for acute gout. Colchicine facilitates the elimination of uric acid from the body. While colchicine is effective, it often causes nausea, vomiting and diarrhea. These side-effects are most common when this drug is taken orally, and because of their unpleasant nature, non-steroidal anti-inflammatory drugs (NSAIDs) have become the treatment of choice for most acute attacks of gout. The NSAID that is most widely used to treat acute gout is indomethacin. NSAIDs also have significant toxicity, but if used for the short-term, are generally well-tolerated.

Therapy directed at normalizing uric acid levels in the blood may be considered for patients who have had multiple gout attacks or who have developed tophi or kidney stones. Several drugs that help the kidneys eliminate uric acid are available, such as probenecid, and a drug that blocks production of uric acid by the body, such as allopurinol. The choice between these two types of drugs depends on the amount of uric acid in the urine.

What is desired are improved formulations for relieving symptoms associated with uric acid crystals that are simple to administer, effective at reducing symptoms, have reduced toxicity, and are less expensive than formulations and treatments that are currently available. What are also needed are formulations for preventing symptoms associated with uric acid crystals in the body.

SUMMARY OF THE INVENTION

I have invented a method for relieving or preventing symptoms associated with uric acid crystals, comprising consuming a formulation that supports three or more processes that reduce a symptom due to uric acid crystals in a body, the processes comprising:
1) a process that inhibits formation of uric acid in the body;
2) a process that increases elimination of uric acid from the body; and
3) a process that interferes with formation of uric acid crystals in the body.

I have also invented a formulation for relieving or preventing symptoms associated with uric acid crystals, comprising: an extract of celery; an extract of cherry; and a lithium salt.

I have also invented a process to make a formulation for relieving or preventing symptoms associated with uric acid crystals, comprising:
a. mixing together:
  i. a material that when consumed inhibits formation of uric acid in a body;
  ii. a material that when consumed increases elimination of uric acid from the body;
  iii. a material that when consumed interferes with formation of uric acid crystals in the body; and
b. forming the mixture of step (a) into a medicament.

DETAILED DESCRIPTION

Additionally, I have invented a formulation for relieving or preventing symptoms associated with uric acid crystals, comprising: three or more food supplements that support three or more processes that reduce uric acid crystals in a body, wherein the formulation is made by a process comprising:
a. making a mixture by combining the three or more food supplements together; and
b. forming the mixture into a medicament.

In one embodiment the method for relieving symptoms associated with uric acid crystals comprises consuming a formulation of an extract of celery, an extract of cherry, and a lithium salt.

An extract is a concentration of the active ingredients in a portion of a leaf, stem, bark, flower, fruit, or seed. Extracts are made by any number of known methods, including steam extraction, alcohol extraction, solvent extraction, and supercritical fluid extraction.

The extract of celery may be from the leaves, stems, seeds, or root of fresh or dried celery. One method to make celery seed extract is described in U.S. Pat. No. 6,761,913. The method includes controlled ethanolic extraction, distillation and drying, and further processing by supercritical fluid extractions (SFE). The celery seed extract may be further fractionated by column fractionation, distillation, LiAlH reduction and the like. The celery seed extract possesses activity for the treatment and prevention of acute and chronic pain, inflammation and gastrointestinal irritation.

The extract of celery inhibits the formation of uric acid in the body. In one embodiment the extract of celery is standardized to contain at least 50% 3-n-butylphthalide calculated as total phthalides. The extract of celery may be standardized to contain any level from at least 15% up to 85%, or even higher, or any amount in between, of 3-n-butylphthalide.

Commercial manufacturers of suitable celery seed extract include Nature's Herbs, Herbal Extracts Plus, Viable Herbal Solutions, and Natural Factors.

The extract of cherry may be from any portion of the fruit or plant, including the leaves, pit, bark, roots, etc. The cherry is from the genus *Prunus*, and may be either sweet cherry (*Prunus avium*), tart cherry (*Prunus cerasus*), Amur choke cherry (*Prunus maackii*), Wild Black Cherry (*Prunus serotina*), or mixtures thereof. In one embodiment the cherry fruit extract is rich in flavonoids. These flavenoids are natural, potent antioxidants which support joint health. Flavonoids have also been shown to support the health of collagen which makes up part of the skin, bones and connective tissue. Cherry fruit extract supports the body's natural anti-inflammatory response, increases the elimination of uric acid from the body, and contains powerful antioxidants to help prevent damage to healthy cells. The extract may be prepared by known extraction, distillation, and purification techniques well known in the art. In one embodiment the extraction is a supercritical fluid extraction. In one embodiment the cherry fruit extract is organic. In one embodiment the extract of cherry is at least a 5:1, an 8:1, a 10:1 concentrate or even higher.

Commercial manufacturers of cherry fruit extract include Enzymatic Therapy Inc., Herbal Extraction Group Inc., Neutraceutical Sciences Institute, and NOW Foods.

Lithium salt is one ingredient that may be used in the formulation which interferes with formation of uric acid crystals in the body. Lithium ions in the blood and urine make the uric acid more soluble so that it doesn't form crystals as readily. Lithium salt may be in any number of different forms, including, but not limited to lithium orotate, lithium proteinate, lithium aspartate, lithium citrate, lithium carbonate, and mixtures thereof.

In one embodiment, the formulation that is used for relieving symptoms associated with uric acid crystals comprises from 25 to 200 mg of extract of celery, from 100 to 1500 mg extract of cherry, and from 1.5 to 10 mg of lithium in the lithium salt in a medicament. The formulation in the medicament is consumed from one to four times a day. The number of times per day can be increased depending on the severity of symptoms.

The medicament is a substrate for providing a single dose of the separate components of, or a mixture of, the complete formulation. The medicament, for example, may be a tablet, a capsule, a pill, a softgel, a suspension, a chewable, a lozenge, or a powder. Thus the formulation may be given in separate medicaments, or in a combined mixture in a single medicament. An advantage of a combined mixture in a single medicament is that a patient consuming the formulation needs to take fewer medicaments, and in some embodiments less inert filler is used in the formulation. In some embodiments the wt % inert filler is less than 10 wt %, less than 5 wt %, or even none at all. Examples of inert fillers are materials also known as excipients. Inert fillers may be used to help bind, preserve, or give bulk to the formulation. Inert fillers may also be used to color, flavor, or change the texture of the formulation.

Capsules are one medicament that can be used. Capsules come in a wide variety of sizes, and there are some that are vegetarian. Some advantages of capsules are that they are generally easy to swallow, dissolve more readily than some other medicaments, and they require lower amounts of (or no amount of) inert filler.

In one embodiment the formulation is a high dose formulation that is effective for relieving the symptoms associated with uric acid crystals during an acute phase of gout. A high dose formulation contains from 100 to 200 mg of extract of celery, from 250 to 1500 mg extract of cherry, and from 3 to 10 mg lithium in the lithium salt, in one or more medicaments. In another embodiment the formulation is a low dose formulation that is effective for preventing the symptoms associated with recurring or chronic gout, kidney stones, or a combination thereof. A low dose formulation contains from 25 to 150 mg of extract of celery, from 100 to 1000 mg of extract of cherry, and from 1.5 to 7.5 mg of lithium in the lithium salt. In one embodiment, the formulation (in one or more medicaments) is consumed one to four times per day.

The method for relieving symptoms associated with uric acid crystals is effective for relieving and preventing the pain symptoms of gout, kidney stones, or combinations thereof.

In one embodiment all the constituents of the formulation are food supplements that are readily available, and have a very low toxicity. In some embodiments the formulation is a mixture of at least three food supplements and is in the form of dry particles, such as a powder, flakes, or granules. In one aspect the formulation is made to a specific blend in a medicament, wherein the medicament is consumed in amounts and at a frequency that is effective for preventing symptoms associated with uric acid crystals, and wherein the medicament is consumed in higher amounts and/or at a higher frequency that is more effective for relieving symptoms associated with uric acid crystals. For example, an individual may take one capsule of the formulation every other day to prevent symptoms and may take one to three capsules of the formulation three times a day to relieve symptoms. The highest dose is selected to assure safety and is adjusted to the specific formulation in the medicament.

One advantage in some embodiments of the invention is that the level of lithium in the formulation is low enough so that when it is consumed in effective amounts it does not require blood monitoring. The level of lithium does not build up to toxic levels, unlike what can occur with earlier known lithium treatments for reducing uric acid crystals in the body. The levels of the lithium salt in the formulation are much lower than what would have been expected to be effective for interfering with formation of uric acid crystals in the body by earlier known methods. This is possible due to the synergistic effect of using a material that inhibits formation of uric acid in a body and a material that increases elimination of uric acid from the body along with the lithium salt.

Another side-benefit of the method of this invention is improved mental functioning caused by improvements in at least two physiochemical processes in the brain. The celery seed extract prevents and improves dementia. The use of n-butylphthalide for this purpose is taught in US Patent Publication 2007/0265336 A1. The lithium stabilizes mood. Tart cherries are also a rich source of melatonin. Besides helping regulate the body's sleep cycle, melatonin is an antioxidant that's able to break through the brain barrier and provide direct antioxidant protection to the delicate structures within brain cells. Melatonin is believed to have strong neuroprotective properties, promoting brain health throughout the aging process.

EXAMPLES

The invention will be further explained by the following illustrative examples that are intended to be non-limiting.

Example 1

The following three dietary supplements were purchased at iHerb:

Natural Factors, Celery Seed Extract, 60 Capsules for $11.97. Each capsule contained 75 mg celery (*Apium graveolens*) seed extract (standardized to contain 85% 3-n-butylphthalide calculated as total phthalides)

Enzymatic Therapy, Cherry Fruit Extract, 180 Capsules for $20.27. Each capsule contained 500 mg of sweet cherry (*Prunus avium*) fruit extract, in a 10:1 concentrate by weight.

Nutrient Carriers Incorporated, Advanced Research, Lithium Orotate, 120 mg, 200 Tablets for $15.00 Each tablet contained 4.9 mg elemental lithium.

A 54 year old man weighing approximately 300 lbs, who was experiencing recurring episodes of gout approximately every few months, was selected for treatment. This man was not known to be taking any other medications at the time of treatment. During one severe episode of gout, the following treatment was provided, and was continued for several months:

1 capsule of celery seed extract—taken three times per day, 1 capsule of cherry fruit extract—taken three times per day, and 1 tablet of lithium orotate—taken twice a day.

The man noticed an improvement in gout symptoms in three to four weeks, and the symptoms let up completely within four to six weeks. The treatment has continued for five months, with no re-occurrence of symptoms and no adverse side-effects. The man attributes the improvement in gout symptoms to the treatment.

Example 2

A 51 year old man weighing approximately 155 lbs, who experienced gout symptoms occasionally (approximately once or twice a year) was selected for treatment. This man was known to be taking multiple food supplements, including 3 gm of Vitamin C and multiple herbs with anti-inflammatory properties, but he was still getting occasional gout symptoms. During one episode of gout pain and inflammation, the following treatment was provided:

4 capsules of celery seed extract—two taken twice per day, 5 capsules of cherry fruit extract—two taken in the morning, one at lunch, and two in the evening, and 3 tablets of lithium orotate—one taken three times a day.

During the first four days of treatment the man in addition took ½ tablet of 0.6 mg colchicine twice a day and massaged the big toe joint with Three Angels Liniment from Blue Poppy Herbs three to four times per day. All the gout symptoms were gone by three days after the initiation of treatment. After four additional days of treatment the treatment was changed to the same treatment as described in Example 1. The man has not experienced any further gout symptoms, or any adverse effects from the treatment, for more than four weeks.

In the past, this man had used medication consisting of a full dose of 50 mg indomethacin three times a day and one tablet twice a day of 0.6 mg colchicine to relieve the symptoms of similar gout pain and inflammation. The gout symptoms would resolve within 3-5 days on this medication regime, but would re-occur within a few months after the medication was discontinued.

Example 3

16 capsules of celery seed extract, 20 capsules of cherry fruit extract, and 12 tablets of lithium orotate are emptied and mixed together in a mortar and pestle. All of the resulting homogeneously mixed powder is placed evenly into 12 empty size 000 gelatin capsules, with no additional filler. Each gelatin capsule thus contains 100 mg celery seed extract, approx. 833 mg cherry fruit extract, and 4.9 mg lithium as lithium orotate.

A patient with gout takes the capsules, 1 capsule with each of 3 meals per day, for two to four days, until all gout symptoms are abated. No NSAIDS nor colchicine are taken during this time, so there is no gastrointestinal distress as a result of the treatment.

Example 4

60 capsules of celery seed extract, 60 capsules of cherry fruit extract, and 40 tablets of lithium orotate are emptied into a food processor. The mixture is processed into a homogeneous fine powder, then filled into 60 clear size 00 vegetarian capsules using a Capsuline®-60 Capsule Filler Machine. A human patient who has had gout in the past, but is currently symptom-free, takes 3 of these filled capsules daily, 1 with each meal. No gout symptoms develop during the period of treatment. No adverse effects of the treatment are felt by the patient. Additionally the patient notices improved mental functioning, including improved sleep, better concentration and memory, and more stable moods after about three months of continued treatment.

We claim:

1. A method for treating gout, comprising orally administering to a subject in need thereof an effective amount of a formulation comprising a synergistic combination of:
   a. 25 to 200 mg celery seed extract;
   b. 100 to 1500 mg cherry (genus *Prunus*) fruit extract; and
   c. 1.5 to 10 mg elemental lithium in a lithium salt;
   wherein the administered formulation relieves gout symptoms in said subject.

2. The method of claim 1, wherein the formulation comprises from 1.5 to 7.5 mg of the elemental lithium.

3. The method of claim 1, wherein the formulation comprises from 1.5 to 4.9 mg of the elemental lithium.

4. The method of claim 3, wherein the formulation comprises from 3 to 4.9 mg of the elemental lithium.

5. The method of claim 2, wherein the lithium salt is selected from the group consisting of lithium orotate, lithium aspartate, lithium proteinate, lithium citrate, lithium carbonate, and mixtures thereof.

6. The method of claim 5, wherein the lithium salt is selected from the group consisting of lithium orotate, lithium aspartate, lithium proteinate, and mixtures thereof.

7. The method of claim 1, wherein the cherry fruit extract is sweet cherry (*Prunus avium*) fruit extract of at least 5:1 concentrate by weight.

8. The method of claim 1, wherein the celery seed extract is standardized to contain at least 50% 3-n-butylphthalide calculated as total phthalides.

9. The method of claim 1, wherein the formulation is consumed from one to four times per day.

10. The method of claim 1, wherein the formulation is administered from once every other day to once per day.

11. The method of claim 1, wherein the symptoms include pain and inflammation.

12. The method of claim 1, wherein the formulation relieves pain and inflammation in said subject.

13. The method of claim 1, wherein the formulation is administered for more than four weeks with no adverse effects on the body.

* * * * *